United States Patent [19]
Blumberg et al.

[11] Patent Number: 5,405,875
[45] Date of Patent: Apr. 11, 1995

[54] METHOD OF INHIBITING NEOPLASIA AND TUMOR PROMOTION

[75] Inventors: Peter M. Blumberg, Frederick; Zoltan Szallasi, Bethesda, both of Md.

[73] Assignee: The United States of America as represented by the Department of Health and Human Services, Washington, D.C.

[21] Appl. No.: 64,251

[22] Filed: May 20, 1993

Related U.S. Application Data

[63] Continuation-in-part of Ser. No. 924,439, Jul. 31, 1992, abandoned, which is a continuation of Ser. No. 681,679, Apr. 8, 1991, abandoned.

[51] Int. Cl.$^6$ ............................................ A61K 31/35
[52] U.S. Cl. .................................. 514/698; 514/689; 514/691
[58] Field of Search ........................ 514/678, 689, 691

[56] References Cited

U.S. PATENT DOCUMENTS 4,716,179 12/1987 Hecker et al. .
5,021,450 6/1991 Blumberg .

OTHER PUBLICATIONS

Aftab et al., "Structure–Activity Relationships of Phenothiazines and Related Drugs for Inhibition of Protein Kinase C," *Molecular Pharmacology*, 40, 798–805 (1991).
Akita et al., "Expression and Properties of Two Distinct Classes of the Phorbol Ester Receptor Family, Four Conventional Protein Kinase C Types, and a Novel Protein Kinase C," *J. Biological Chemistry*, 265(1) 354–362 (Jan. 1990).
Baird et al., "Tumor-promoting Activity of Phorbol and Four Diesters of Phorbol in Mouse Skin," *Cancer Research*, 31, 1074–79 (Aug. 1971).
Berry et al., "Metabolic Conversion of 12-O-Tetradecanoylphorbol-13-acetate in Adult and Newborn Mouse Skin and Mouse Liver Microsomes," *Cancer Research*, 38, 2301–06 (Aug. 1978).
Binder et al., "Characterization of the Induction of Ornithine Decarboxylase Activity by Benzoyl Peroxide in SENCAR Mouse Epidermis," *Carcinogenesis*, 10(12), 2351–57 (1989).
Blumberg et al., "Specific Receptors for Phorbol Ester Tumor Promoters and Their Involvement in Biological Responses" (Chapter 5) in *Mechanisms of Tumor Promotion* (vol. III) (Thomas J. Slaga, ed., CRC Press, Inc., Boca Raton, Fla. 1984).
Blumberg, "Protein Kinase C as the Receptor for the Phorbol Ester Tumor Promoters: Sixth Rhoads Memorial Award Lecture" *Cancer Research*, 48, 1–8 (Jan. 1988).
Blumberg, "Complexities of the Protein Kinase C Pathway," *Mol. Carcinog.*, 4, 339–344 (1991).
Blumberg et al., "The Bryostatins, A Family of Protein Kinase C Activators with Therapeutic Potential" in *New Leads and Targets in Drug Research*, 273–285 (Krogsgaard–Larsen et al., eds., Alfred Benzon Symposium 33, Munksgaard, Copenhagen 1992).
Campbell, "Lipid–Derived Autacoids: Eicosanoids and Platelet-Activating Factor" (Chapter 24) in *Goodman and Gilman's The Pharmacological Basis of Therapeutics*, 8th Ed. (Gilman et al., ed., Pergamon Press, New York 1990).
Cashmore et al., "The Structure of Prostratin: A Toxic Tetracyclic Diterpene Ester from Pimelea Prostrata," *Tetrahedron Lett.*, 1737–1738 (1976).

(List continued on next page.)

Primary Examiner—Johann Richter
Assistant Examiner—John Peabody
Attorney, Agent, or Firm—Leydig, Voit & Mayer, Ltd.

[57] ABSTRACT

The present invention provides a method of inhibiting neoplasia and tumor promotion. The method comprises administering to a mammal, particularly a human, in need thereof an effective amount of a 12-deoxyphorbol ester, particularly a 12-deoxyphorbol 13-monoester such as 12-deoxyphorbol 13-acetate (prostratin) and 12-deoxyphorbol 13-phenylacetate (dPP).

8 Claims, 5 Drawing Sheets

OTHER PUBLICATIONS

Casnellie, "Protein Kinase Inhibitors: Probees for the Functions of Protein Phosphorylation," *Advances in Pharmacology*, 22, 167-71 (1991).

DiGiovanni et al., "Structure-Activity Relationships for Epidermal Ornithine Decarboxylase Induction and Skin Tumor Promotion by Anthrones," *Carcinogenesis*, 9(8), 1437-43 (1988).

Driedger et al., "Structure-Activity Relationships in Chick Embryo Fibroblasts for Phorbol-related Diterpene Esters Showing Anomalous Activities in Vivo," *Cancer Res.*, 40, 339-346 (1980).

Dunn et al., "Specific Binding of [20-$^3$H]12-Deoxyphorbol 13-Isobutyrate to Phorbol Ester Receptor Subclasses in Mouse Skin Particulate Preparations," *Cancer Research*, 43, 4632-37 (Oct. 1983).

Ellis et al., "Activation of Protein Kinase C by Tumor-Promoting and Non-Promoting Phorbol Esters," *J. Pharmacy and Pharmacology*, 37, 23P (Dec. 1985).

Fischer et al., "Correlation of Phorbol Ester Promotion in the Resistant C57BL/6J Mouse with Sustained Hyperplasia But Not Ornithine Decarboxylase or Protein Kinase C," *Cancer Res.*, 49, 6693-6699 (1989).

Fürstenberger et al., "Skin Tumor Promotion by Phorbol Esters Is A Two-Stage Process," *Proc. Natl. Acad. Sci. USA*, 78(12), 7722-26 (Dec. 1981).

Goth, "Drug-Receptor Interactions" (Chapter 2) in *Medical Pharmacology Principles and Concepts*, 10th Ed. (The C.V. Mosby Company, St. Louis 1981).

Gschwendt et al., "Bryostatin 1, An Activator of Protein Kinase C, Mimics As Well As Inhibits Biological Effects of the Phorbol Ester TPA in vivo and in vitro," Carcinogenesis, 9(4), 555-62 (1988).

Gustafson et al., "A Nonpromoting Phorbol from the Samoan Medicinal Plant *Homalanthus nutans* Inhibits Cell Killing by HIV-1," *J. Med. Chem.*, 35, 1978-1986 (1992).

Hecker, "Cocarciogens from Euphorbiaceae and Thymeleaceae" in *Symposium on Pharmacognosy and Phytochemistry*, 147-165 (Wagner et al., eds., Springer Verlag 1970).

Hecker, "Structure-Activity Relationships in Diterpene Esters Irritant and Cocarcinogenic to Mouse Skin" in *Carcinogenesis, vol. 2. Mechanisms of Tumor-Promotion and Carcinogenesis*, 11-47 (Slaga et al., eds., Raven Press, New York 1978).

Hegemann et al., "The Antipsoriatic Drug, Anthralin, Inhibits Protein Kinase C—Implications for Its Mechanism of Action," *Arch. Dermatol. Res.*, 284, 179-183 1992).

Hennings et al., "Bryostatin 1, An Activator of Protein Kinase C, Inhibits Tumor Promotion by Phorbol Esters in SENCAR Mouse Skin," *Carcinogenesis*, 8(9), 1343-46 (1987).

Hergenhahn et al., "Biological Assays for Irritant Tumor-initiating and -promoting Activities," *J. Cancer Res. Clin. Oncol.*, 104, 31-39 (1982).

Insel, "Angalgesic α Antipyretics and Antiinflammatory Agents; Drugs Employed in the Treatment of Rheumatoid Arthritis and Gout" (Chapter 26) in *Goodman and Gilman's The Pharmacological Basis of Therapeutics*, 8th Ed. (Gilman et al., ed., Pergamon Press, New York 1990).

Irie et al., "Structure—Activity Studies of the Indole Alkaloid Tumor Promoter Teleocidins," *Carcinogenesis*, 8(4), 547-552 (1987).

Kazanietz eta l., "Differential Irreversible Insertion of Protein Kinase C into Phospholipid Vesicles by Phorbol Esters and Related Activators," *J. Biol. Chem.*, 267(29), 20878-20886 (1992).

Klein-Szanto, "Morphological Evaluation of Tumor Promoter Effects on Mammalian Skin" (Chapter 3) in *Mechanism of Tumor Promotion* (vol. II) (Thomas J. Slaga, ed., CRC Press, Inc., Boca Raton, Fla. 1984).

Lichti et al., "Genetic Evidence That a Phorbol Ester Tumor Promoter Stimulates Ornithine Decarboxylase Activity by a Pathway That Is Independent of Cyclic AMP-Dependent Protein Kinases in CHO Cells," *J. Cellular Physiology*, 113, 433-39 (1982).

Madri, "Inflammation and Healing" (Chapter 2) in *Anderson's Pathology*, 9th Ed. (Kissane, ed., The C.V. Mosby Company, St. Louis 1990).

Nishizuka, "The Role of Protein Kinase C in Cell Surface Signal Transduction and Tumour Promotion," *Nature*, 308(19), 693-98 (Apr. 1984).

Nishizuka, "Studies and Perspectives of Protein Kinase C," *Science*, 233, 305-12 (Jul. 1986).

Nishizuka, "The Molecular Heterogeneity of Protein Kinase C and Its Implications for Cellular Regulation," *Nature*, 334(25), 661-65 (Aug. 1988).

Nishizuka, "Studies and Prospectives of the Protein (List continued on next page.)

OTHER PUBLICATIONS

Kinase C Family for Cellular Regulation," *Cancer*, 63, 1892–1903 (May 1989).

Nishizuka, "Intracellular Signaling by Hydrolysis of Phospholipids and Activation of Protein Kinase C," *Science*, 258, 607–614 (1992).

O'Brien et al., "Induction of the Polyamine–biosynthetic Enzymes in Mouse Epidermis by Tumor–promoting Agents," *Cancer Research*, 35, 1662–70 (Jul. 1975).

Sako et al., "Partial Parallelism and Partial Blockade by Bryostatin 1 of Effects of Phorbol Ester Tumor Promoters on Primary Mouse Epidermal Cells," *Cancer Research*, 47, 5445–50 (Oct. 1987).

Schmidt et al., "Simple Phorbol Esters as Inhibitors of Tumor Promotion by TPA in Mouse Skin," in *Carcinogenesis and Biological Effects of Tumor Promoters*, 7, 57–63 (Hecker et al., eds., Raven Press, New York 1982).

Scribner et al., "Inflammation and Tumor Promotion: Selective Protein Induction in Mouse Skin by Tumor Promoters," *Europ. J. Cancer*, 8, 617–621 (1972).

Sekiguchi et al., "Three Distinct Forms of Rat Brain Protein Kinase C: Differential Response to Unsaturated Fatty Acids," *Biochemical and Biophysical Research Communications*, 145(2), 797–802 (Jun. 1987).

Sisskin et al., "Correlation Between Sensitivity to Tumor Promotion and Sustained Epidermal Hyperplasia of Mice and Rats Treated with 12–O–tetradecanoylphorbol–13–acetate," *Carcinogenesis*, 3(4), 403–407 (1982).

Slaga et al., "Studies on the Mechanism of Skin Tumor Promotion: Evidence for Several Stages in Promotion," *Proc. Natl. Acad. Sci. USA*, 77(6), 3659–3663 (Jun. 1980).

Slaga et al., "Overview of Tumor Promotion in Animals," *Environmental Health Perspective*, 50, 3–14 (1983).

Stanley et al., "Mouse Skin Inflammation Induced by Multiple Topical Applications of 12–O–Tetradecanoylphorbol–13–Acetate," *Skin Pharmacol.*, 4, 262–71 (1991).

Szallasi et al., "Prostratin, a Nonpromoting Phorbol Ester, Inhibits Induction by Phorbol 12–Myristate 13–Acetate of Ornithine Decarboxylase, Edema, and Hyperplasia in CD–1 Mouse Skin" *Cancer Research*, 51, 5355–60 (Oct. 1991).

Szallasi et al., "Non–Promoting 12–deoxyphorbol 13–3sters as Potent Inhibitors of Phorbol 12–myristate 13–acetate–induced Acute and Chronic Biological Responses in CD–1 Mouse Skin," *Carcinogenesis*, 13(11), 2161–67 (1992).

Szallasi et al., "Neurogenic Component of Phorbol Ester–induced Mouse Skin Inflammation," *Cancer Res.*, 49, 6052–6057 (1989).

Verma et al., "Induction of Mouse Epidermal Ornithine Decarboxylase Activity and DNA Synthesis by Ultraviolet Light," *Cancer Research*, 39, 1035–40 (Mar. 1979).

Wennogle et al., "Profiling of Inhibitors of Protein Kinase C," *Adv. Enz. Regulation*, 27, 287–93 (1988).

Westwick et al., "Structure Activity Relationships of 12–Deoxyphorbol Esters on Human Platelets," *Thromb. Res.*, 20, 683–692 (1980).

Yeh et al., "Influence of Side Chains on Phorbol Ester Binding to Protein Kinase C," *Chemical Abstracts*, 109, 88635p (1988).

Young et al., "Tachyphylaxis in 12–O–Tetradecanoylphorbol Acetate–and Arachidonic Acid–Induced Ear Edema," *J. Investigative Dermatology*, 80, 48–52 (1983).

Zayed et al., "Structure Activity Relations of Polyfunctional Diterpenes of the Tigliane Type, VI," *Planta Medica*, 34, 65–69 (Feb. 1984).

Ogura et al., *Planta Medica*, 33 (2), 128–143 (1978).

METHOD OF INHIBITING NEOPLASIA AND TUMOR PROMOTION

This patent application is a continuation-in-part of U.S. patent application Ser. No. 07/924,439, filed on Jul. 31, 1992, which, in turn, is a continuation of U.S. patent application Ser. No. 07/681,679, filed on Apr. 8, 1991, now abandoned.

TECHNICAL FIELD OF THE INVENTION

The present invention relates to the inhibition of neoplasia and tumor promotion, particularly the use of phorbol diterpenes to inhibit neoplasia and tumor promotion.

BACKGROUND OF THE INVENTION

Many compounds have been identified as carcinogenic agents, particularly neoplasia and tumor promoters. In the study of the mechanism of neoplasia and tumor promotion, phorbol esters have received particular attention and are characterized as extremely potent tumor promotion agents (Blumberg et al., "Specific Receptors for Phorbol Ester Tumor Promoters and Their Involvement in Biological Responses" (Chapter 5) in *Mechanisms of Tumor Promotion* (Volume III) (Thomas J. Slaga, ed., CRC Press, Inc., Boca Raton, Fla. 1984)).

Some phorbol compounds, however, have also been disclosed as useful in the inhibition of neoplasia and tumor promotion. The diterpene alcohol phorbol has been disclosed as an antineoplastic agent (U.S. Pat. No. 4,716,179), and the phorbol derivatives phorbol-12,13-diacetate (PDA), phorbol-12,13-dipropionate (PDPr), phorbol-12,13-dibutyrate (PDBu), phorbol-12,13-dibenzoate (PDB), and phorbol 12,13,20-triester (PTA) have been disclosed as inhibiting tumor promotion by the tumor promoter 12-O-tetradecanoylphorbol-13-acetate (TPA) in 7,12-dimethylbenzanthracene (DMBA)-initiated mouse skin (Schmidt et al., "Simple Phorbol Esters as Inhibitors of Tumor Promotion by TPA in Mouse Skin," in *Carcinogenesis and Biological Effects of Tumor Promotors*, 7, 57–63 (Hecker et al., eds., Raven Press, New York 1982)). The disclosed results regarding the phorbol derivatives, however, have not been replicated, and no inhibition of neoplasia and tumor promotion by TPA by these phorbol derivatives was found in a different mouse strain (Slaga et al., "Studies on the Mechanism of Skin Tumor Promotion: Evidence for Several Stages in Promotion," *Proc. Natl. Acad. Sci. USA*, 77(6), 3659–3663 (June 1980)). Moreover, the results indicating the inhibition of tumor promotion are inconsistent with the disclosure that PDB and PDBu are tumor promoters (Baird et al., *Cancer Res.*, 31, 1074–1079 (1971); Thielman et al., in *Fortschritte der Krebsforschung*, 7, 171–179 (Schmidt et al., eds., Schattauer, Stuttgart 1969)) and the general view that the tumor promoting actions of phorbol derivatives are additive and do not cancel each other (Driedger et al., *Cancer Res.*, 40, 339–346 (1980)).

Thus, there remains a need for effective inhibitors of neoplasia and tumor promotion, particularly such inhibitors which do not have adverse side-effects and can be safely applied to mammals, especially humans. The present invention provides such inhibitors of neoplasia and tumor promoters, including the potent tumor promoter of the phorbol ester class TPA, which is also known as phorbol 12-myristate 13-acetate (PMA).

These and other objects and advantages of the present invention, as well as additional inventive features, will be apparent from the description of the invention provided herein.

BRIEF SUMMARY OF THE INVENTION

The present invention provides a method of inhibiting neoplasia and tumor promotion. The method comprises administering to a mammal, particularly a human, in need thereof an effective amount of a 12-deoxyphorbol 13-monoester such as 12-deoxyphorbol 13-acetate (prostratin) and 12-deoxyphorbol 13-phenylacetate (dPP).

BRIEF DESCRIPTION OF THE DRAWINGS

FIG. 1A is a plot of the percent of mice with papillomas versus weeks of treatment, while FIG. 1B is a plot of the number of papillomas per mouse versus weeks of treatment. The data points are for various groups of mice in a first set of experiments.

FIGS. 2A and 2C are plots of the percent of mice with papillomas versus weeks of treatment, while FIGS. 2B and 2D are plots of the number of papillomas per mouse versus weeks of treatment. The data points are for various groups of mice in a second set of experiments.

FIGS. 3A and 3B are plots of the number of papillomas per mouse versus pretreatment dose of prostratin and dPP, respectively. The data points are for pooled similar groups of mice in the first and second sets of experiments.

FIG. 4A is a plot of the percent of mice with papillomas versus weeks of treatment, while FIG. 4B is a plot of the number of papillomas per mouse versus weeks of treatment. The data points are for various groups of mice in third and fourth sets of experiments.

DESCRIPTION OF THE PREFERRED EMBODIMENTS

Figure 1A:
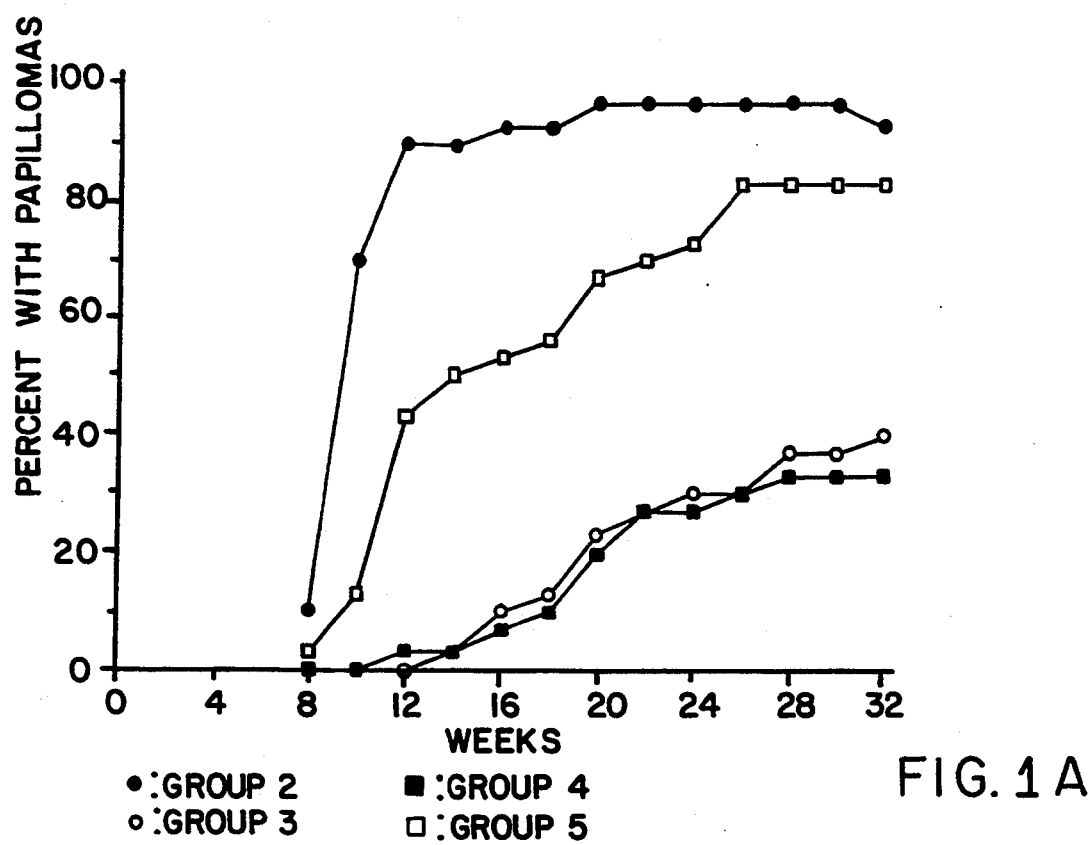
FIGS. 1A and 1B are graphs illustrating the inhibition by prostratin of tumor promotion.

The present invention is predicated on the surprising discovery that 12-deoxyphorbol 13-monoesters not only are not tumor promoting but are inhibitors of neoplasia and tumor promotion. The present invention, therefore, provides a method of inhibiting neoplasia and tumor promotion comprising administering to a mammal, particularly a human, in need thereof an effective amount of a 12-deoxyphorbol 13-monoester. The 12-deoxyphorbol 13-monoester is preferably one in which the ester is selected from the group consisting of formate, acetate, propionate, butyrate, pentanoate, hexanoate, benzoate, and phenylacetate. Most preferably, 12-deoxyphorbol 13-monoester is the 12-deoxyphorbol 13-acetate (prostratin) or 12-deoxyphorbol 13-phenylacetate (dPP). The 12-deoxyphorbol 13-monoester may be administered in any suitable manner, most typically with a pharmaceutically acceptable carrier.

The 12-deoxyphorbol 13-monoesters exemplified by prostratin and dPP form a new class of protein kinase C (PKC) activators of unique biological activity. Although they bind to and activate PKC, in mouse skin they either fail to induce typical phorbol ester (PMA)

effects (e.g., hyperplasia) or induce only partial response (e.g., inflammation). Furthermore, pretreatment with these agents inhibits a range of PMA induced effects (acute and chronic hyperplasia, inflammation, etc.). The subject compounds reduce both the average number of papillomas and the tumor incidence in a tumor promotion schedule in CD-1 mouse skin, in which each PMA application was preceded by 12-deoxyphorbol monoester pretreatment, thereby demonstrating the in vivo efficacy of the present invention in animals, including humans. The highest dose of prostratin used (2.56 μmol or 1 mg/pretreatment) caused a 96% (23-fold) reduction in the average number of papillomas with a decrease of tumor incidence from 97% to 40%. The highest dose of dPP used (21.4 nmol or 10 μg/pretreatment) induced an 86% (7-fold) reduction in the average number of papillomas with a reduction of tumor incidence from 100% to 47%. The inhibitory effect was dose dependent, and the $ID_{50}$ was 11 nmol/-pretreatment for prostratin and 0.8 nmol/pretreatment for dPP. Maximal inhibition of tumor promotion was accompanied by a block of epidermal hyperplasia; however, significant inhibition of tumor induction was observed at doses without any apparent effect on the PMA induced hyperplasia.

The Action of Phorbol Esters

The phorbol esters have been the object of intense research effort, initially driven by the potent neoplasia and tumor promoting activity of these compounds in mouse skin. These investigations revealed that the major receptor for the phorbol esters is protein kinase C (PKC), a family of serine/threonine kinases involved in cellular signal transduction (Nishizuka, *Nature*, 308, 693-698 (1984); Nishizuka, *Science*, 233, 305-312 (1986); Nishizuka, *Nature*, 334, 661-665 (1988); and Nishizuka, *Science*, 258, 607-614 (1992 )) . The phorbol esters function as ultrapotent analogs of sn-1,2 -diacylglycerol, the lipophilic second messenger generated through hydrolysis of phosphatidylinositol 4,5-biphosphate and phosphatidylcholine (Blumberg, *Cancer Res.*, 48, 1-8 (1988)). This signalling pathway is of central importance in control of cellular growth and differentiation and is a target of multiple oncogenes (Blumberg, *Mol. Carcinog.*, 4, 339-344 (1991)).

One strategy for dissecting the complexity of control of the protein kinase C pathway has been to exploit differences among phorbol esters and related natural products in the patterns of biological response which they induce (Blumberg, *Mol. Carcinog.*, 4, 339-344 (1991)). The existence of such differences was an early finding (Hergenhahn et al., *J. Cancer Res. Clin. Oncol.*, 104, 31-39 (1982); Hecker, "Structure-Activity Relationships in Diterpene Esters Irritant and Co-Carcinogenic to Mouse Skin" in *Mechanisms of Tumor-Promotion and Carcinogenesis*, 11-47 (Slaga et al., eds., Raven Press, New York 1978)). The most dramatic example of divergent responses is provided by the bryostatins. These compounds, while yet more potent activators of protein kinase C in vitro than the phorbol esters, induce only a subset of responses typical of the phorbol esters and block in a dominant fashion those responses which they themselves do not induce (Blumberg et al., "The Bryostatins, A Family of Protein Kinase C Activators with Therapeutic Potential" in *New Leads and Targets in Drug Research*, 273-285 (Krogsgaard-Larsen et al., eds., Alfred Benzon Symposium 33, Munksgaard, Copenhagen 1992)).

Recently, a second class of protein kinase C activators has emerged which, like the bryostatins, function at the biological level as partial antagonists, namely the 12-deoxyphorbol 13-monoesters (Zayed et al., *Planta Med.*, 34, 65-69 (1984)). Whereas 12-deoxyphorbol 13-tetradecanoate was potent both for mouse ear reddening and for tumor promotion, shorter chain derivatives were found to be irritating but not promoting (Zayed et al., *Planta Med.*, 34, 65-69 (1984)), leading to the conclusion that these biological activities had to be considered as virtually independent (Hecker, "Cocarcinogens from Euphorbiaceae and Thymeleaceae" in *Symposium on Pharmacognosy and Phytochemistry*, 147-165 (Wagner et al., eds., Springer Verlag 1970)). Initial analysis of short chain 12-deoxyphorbol derivatives in cellular systems, however, failed to reveal unique behavior (Westwick et al., *Thromb. Res.*, 20, 683-692 (1980); Driedger et al., *Cancer Res.*, 40, 339-346 (1980)).

Prostratin has been identified as the constituent in the Samoan medicinal plant *Humolanthus nutans*, which is responsible for its activity in a screen for anti-HIV agents (Gustafson et al., *J. Med. Chem.*, 35, 1978-1986 (1992)). Prostratin had been previously identified as a toxic constitute of *Pimelea prostrata* (Cashmore et al., *Tetrahedron Lett.*, 1737-1738 (1976)). It was reported to be 144-fold less potent than PMA for mouse ear reddening and, at a dose 40-fold that of PMA, not to be tumor promoting (Zayed et al., *Planta Med.*, 34, 65-69 (1984)). In mouse skin, prostratin functioned as a partial agonist, inducing ornithine decarboxylase and myeloperoxidase (a marker of neutrophil granulocyte infiltration) only to 25-30% of the level induced by PMA (Gustafson et al., *J. Med. Chem.*, 35, 1978-1986 (1992)). No hyperplasia was observed either in response to single or multiple treatments, and keratin K6, a marker of hyperproliferation, was not induced (Szallasi et al., *Cancer Res.*, 51, 5355-5360 (1991); Szallasi et al., *Carcinogenesis*, 13, 2161-2167 (1992)).

By analogy with the bryostatins, it was assumed that perhaps the partial or complete lack of response reflected suppression of the protein kinase C pathway by prostratin. Indeed, pretreatment with prostratin fully suppressed PMA-induced acute and chronic hyperplasia, induction of ornithine decarboxylase, and keratin K6 expression (Szallasi et al., *Cancer Res.*, 51, 5355-5360 (1991) and Szallasi et al., *Carcinogenesis* 13, 2161-2167 (1992)). Edema and myeloperoxidase were reduced approximately 70% (Szallasi et al., *Cancer Res.*, 51, 5355-5360 (1991) and Szallasi et al., *Carcinogenesis*, 13, 2161-2167 (1992)). The effectiveness of prostratin significantly depended on the pretreatment schedule. An optimal schedule was treatment with 256 nmol prostratin 24-48 hrs before PMA application and with 2.56 μmol prostratin 15 min before PMA application. Curiously, a higher dose of prostratin for the initial treatment was less effective (Szallasi et al., *Carcinogenesis*, 13, 2161-2167 (1992)).

Because prostratin displayed relatively low potency, dPP was also evaluated. dPP is comparably potent to PMA for mouse ear reddening (Hergenhahn et al., *J. Cancer Res. Clin. Oncol.*, 104, 31-39 (1982)), although it shows markedly different kinetics (Szallasi et al., *Cancer Res.*, 49, 6052-6057 (1989)). In mouse skin, dPP behaved, in general, similarly to prostratin, both for induction of acute responses and for inhibition of response to PMA, but with 100-fold greater potency. Interestingly, however, the suppression of PMA induced chronic hyperplasia was incomplete (Szallasi et al., *Carcinogenesis* 13, 2161-2167 (1992)).

Chronic hyperplasia is considered the best correlate of tumor promoting activity in mouse skin (Sisskin et al., *Carcinogenesis*, 3, 403-407 (1982); Fischer et al., *Cancer Res.*, 49, 6693-6699 (1989)). Thus, the suppression of hyperplasia by prostratin was arguably a strong predictor that prostratin would be an anti-tumor promoting phorbol ester; however, the suppression of hyperplasia did not reasonably prove such to be the case, particularly since others had reached contrary conclusions regarding the relationship of hyperplasia and tumor effects (Klein-Szanto, "Morphological Evaluation of Tumor Promoter Effects on Mammalian Skin" (Chapter 3) in *Mechanisms of Tumor Promotion* (Volume II) (Thomas J. Slaga, ed., CRC Press, Inc., Boca Raton, Fla. 1984)).

Inhibition of Neoplasia and Tumor Promotion Mechanism

The discovery that 12-deoxyphorbol 13-monoesters such as prostratin and dPP act as inhibitors of neoplasia and tumor promotion dramatically extends the range of behavior previously described for phorbol ester congeners. Whereas variation in the effectiveness of phorbol derivatives as tumor promoters has achieved acceptance (Hecker, "Structure-Activity Relationships in Diterpene Esters Irritant and Co-Carcinogenic to Mouse Skin" in *Mechanisms of Tumor-Promotion and Carcinogenesis* 11-47 (Slaga et al., eds., Raven Press, New York 1978)), prostratin and dPP provide the first persuasive examples for anti-promotion. In addition, the findings underlying the present invention provide great confidence that the failure to observe promotion by prostratin is not simply a consequence of an inadequate dosage level. Earlier findings with bryostatin, which unambiguously antagonizes a subset of phorbol ester responses in intact cells (Sako et al., *Cancer Res.*, 47, 5445-5450 (1987)), yielded only limited evidence for inhibition of promotion (Hennings et al., *Carcinogenesis*, 8, 1343-1346 (1987); Gschwendt et al., *Carcinogenesis*, 9, 555-562 (1988)). The impressive antagonism of PMA promotion in NMRI mice by short-chain phorbol diesters remains the one other example of such antagonism in the literature (Schmidt et al., "Simple Phorbol Esters As Inhibitors of Tumor Promotion by TPA in Mouse Skin" in *Carcinogenesis and Biological Effects of Tumor Promoters*, 57-63 (Hecker et al., eds., Raven Press, New York 1982)). Unfortunately, this latter report has not been independently verified, and several of the compounds are either themselves promoting or are not anti-promoting in other mouse strains (Slaga et al., *Proc. Natl. Acad. Sci. USA*, 77, 3659-3663 (1980); Scribner et al., *Europ. J. Cancer*, 8, 617-621 (1972); Baird et al., *Cancer Res.*, 31, 1074-1079 (1971)). An examination of such short-chain substituted phorbol diesters revealed that they do not inhibit hyperplasia, in contrast to the 12-deoxyphorbol 13-monoesters which are the subject of the present inventive method (Szallasi et al., *Carcinogenesis* 13, 2161-2167 (1992)).

The mechanism for the antagonism of promotion remains to be determined. In vitro studies were carried out, but they reveal that prostratin and dPP show little selectivity for high affinity binding between protein kinase C isozymes $\alpha$, $\beta$, $\gamma$, $\delta$, $\epsilon$, and $\eta$. On the other hand, it has been previously reported that protein kinase C shows two functional binding sites for phorbol esters with distinct structure-activity relations (Kazanietz et al., *J. Biol. Chem.*, 267, 20878-20886 (1992)). The 12-deoxyphorbol 13-monoesters show differentially weak affinity for the secondary site involved in insertion of protein kinase C into the membrane (Kazanietz et al., *J. Biol. Chem.*, 267, 20878-20886 (1992)). In addition, in several cell types including mouse primary epidermal cells, prostratin and dPP show selective downregulation of PKC$\delta$ compared to PKC$\alpha$, in contrast to PMA. Emerging evidence indicates that different protein kinase C isozymes fulfill different cellular functions. In rat basophilic leukemia RBL-2H3 cells, for example, protein kinase C isozymes $\beta$ and $\delta$ reconstitute the secretory response, whereas protein kinase C isozymes $\alpha$ and $\epsilon$ modulate phosphatidylinositol hydrolysis. While the precise model for the anti-promoting activity of 12-deoxyphorbol 13-monoesters is unknown, at least in concept, differential downregulation of isozymes with distinct biological functions provides a plausible model; however, the present invention is not to be limited with respect to any particular perceived anti-promoting model.

Because of its central role in cellular signal transduction, protein kinase C represents an attractive target for therapeutic intervention. The difficult issue has been how to achieve selectivity. The present invention, together with the earlier work with bryostatin (Blumberg et al., "The Bryostatins, A Family of Protein Kinase C Activators with Therapeutic Potential" in *New Leads and Targets in Drug Research*, 273-285 (Krogsgaard-Larsen et al., eds., Alfred Benzon Symposium 33, Munksgaard, Copenhagen 1992), demonstrates that dissection of subpathways of protein kinase C response is possible. Anti-cancer agents targeted to the regulatory domain of protein kinase C have proven to be a successful strategy, complementing efforts to obtain selectivity for the catalytic domain. The concept that protein kinase C activators are necessarily tumor promoters and, therefore, unsuitable as therapeutic agents is no longer a valid one.

Formulations

The 12-deoxyphorbol 13-monoesters employed in the present invention may be used alone or in appropriate association, and also may be used in combination with other pharmaceutically active compounds. The active agent may be present in the pharmaceutical composition in any suitable quantity. The pharmaceutically acceptable excipients described herein, for example, vehicles, adjuvants, carriers or diluents, are readily available to the public.

While the method of the present invention can be practiced in vitro, it has particular usefulness in in vivo applications. As regards these applications, the present inventive method includes the administration to an animal, particularly a mammal, and most particularly a human, of a therapeutically effective amount of one or more of the aforementioned 12-deoxyphorbol 13-monoesters as an active agent effective in the inhibition of neoplasia and tumor promotion, as well as pharmaceutically acceptable derivatives and salts thereof.

One skilled in the art will appreciate that suitable methods of administering a compound of the present invention to an animal are available, and, although more than one route can be used to administer a particular compound, a particular route can provide a more immediate and more effective reaction than another route. Pharmaceutically acceptable excipients are also well-known to those who are skilled in the art, and are readily available. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels, and the like containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Administration

The dose administered to an animal, particularly a human, in the context of the present invention should be sufficient to effect a prophylactic or therapeutic response in the animal over a reasonable time frame. One skilled in the art will recognize that dosage will depend upon a variety of factors including the strength of the particular compound employed, the condition of the animal, the body weight of the animal, as well as the severity and stage of the neoplasia and tumor promotion. Most typically, the compounds employed in the present inventive method will be administered to the surface of tissue, e.g., topically to skin and internally to the gastrointestinal tract, nasal passages, and lung. Thus, the administered dose will generally need to take into account the surface area of the tissue to be treated.

The size of the dose will also be determined by the existence, nature, and extent of any adverse side-effects that might accompany the administration of a particular compound. Suitable doses and dosage regimens can be determined by comparisons to other anti-neoplasia and anti-tumor compounds known to effect the desired response. Specifically, a suitable dose is that which will result in a concentration of the active agent (typically on the surface of tissue) which is known to effect the desired response. The preferred dosage is the amount which results in maximum inhibition of neoplasia and tumor promotion, without significant side effects.

An effective amount of the compounds employed in the present invention is that amount which is sufficient to elicit some inhibition response in neoplasia and tumor promotion in a particular animal. In proper doses and with suitable administration of certain compounds, the present invention provides for a wide range of the inhibition of neoplasia and tumor promotion, e.g., from little inhibition of neoplasia and tumor promotion to essentially full inhibition of neoplasia and tumor promotion. Typical doses include about 1–100,000 nmol prostratin/ml carrier and about 0.1–10,000 nmol dPP/ml carrier, more typically about 10–50,000 nmol prostratin/ml carrier and about 1–5,000 nmol dPP/ml carrier, most typically about 1,000–30,000 nmol prostratin/ml carrier and about 10–3,000 nmol dPP/ml carrier.

Examples

The following examples further illustrate the present invention but, of course, should not be construed as in any way limiting its scope.

Example 1

This example demonstrates the in vivo efficacy of the present inventive method by illustrating the inhibition by prostratin of neoplasia and tumor promotion in animals.

Female Charles River CD-1 mice, 5 weeks of age, were obtained from Charles River Laboratories, Wilmington, Mass. The animals were shaved at 6 weeks of age, and mice in the resting phase of the hair cycle were used for tumor promotion experiments. DMBA was obtained from Eastman, Rochester, N.Y. PMA, prostratin, and dPP were obtained from LC Services, Woburn, Mass. The prostratin was repurified before use.

Seven groups of 30 mice each were established (groups 1–7). The mice were subjected to a treatment schedule consisting of initiation (day 1), pretreatment (day 15), and promotion with two compounds (weeks 3–22; twice/week; 15 minute difference between the treatments with the two compounds in the designated order; beginning with day 17). The initiation involved the topical administration to the mice of either 20 nmol (50 μg) of dimethylbenzanthracene (DMBA, a known carcinogen) dissolved in 200 μl of acetone or merely 200 μl acetone (a carrier material which is not a carcinogen). The pretreatment involved administering to the mice either 100 μl acetone or 256 nmol prostratin. The promotion involved the administration of various combinations and concentrations of acetone, PMA, and prostratin to the initiated skin area. The DMBA was applied in 200 μl acetone, while all other treatments were applied in 100 μl acetone. The precise treatment schedule is set forth in Table 1. The employed treatment schedule was based on the most effective protocol inhibiting PMA induced chronic hyperplasia (Szallasi et al., Cancer Res., 51, 5355–5360 (1991) and Szallasi et al., Carcinogenesis, 13, 2161–2167 (1992)), i.e., all mice were pretreated two days before the first PMA treatment (the beginning of the promotion) and during the promotion period every single PMA treatment was preceded by a corresponding prostratin pretreatment at a 15 min interval.

vals with the following doese: (●) 100 μl acetone/8.1 nmol PMA (group 2), (○) 2.56 μmol prostratin/8.1 nmol PMA (group 3), (⊙) 256 nmol prostratin/8.1 nmol PMA (group 4), and (□) 25.6 nmol prostratin/8.1 nmol PMA (group 5). The percent with papillomas is defined as the percentage of surviving animals bearing one or more papillomas at every second week (FIG. 1A), while the number of papillomas per mouse is defined as the total number of papillomas counted divided by the total number of mice surviving every second week (FIG. 1B).

Figure 1B:
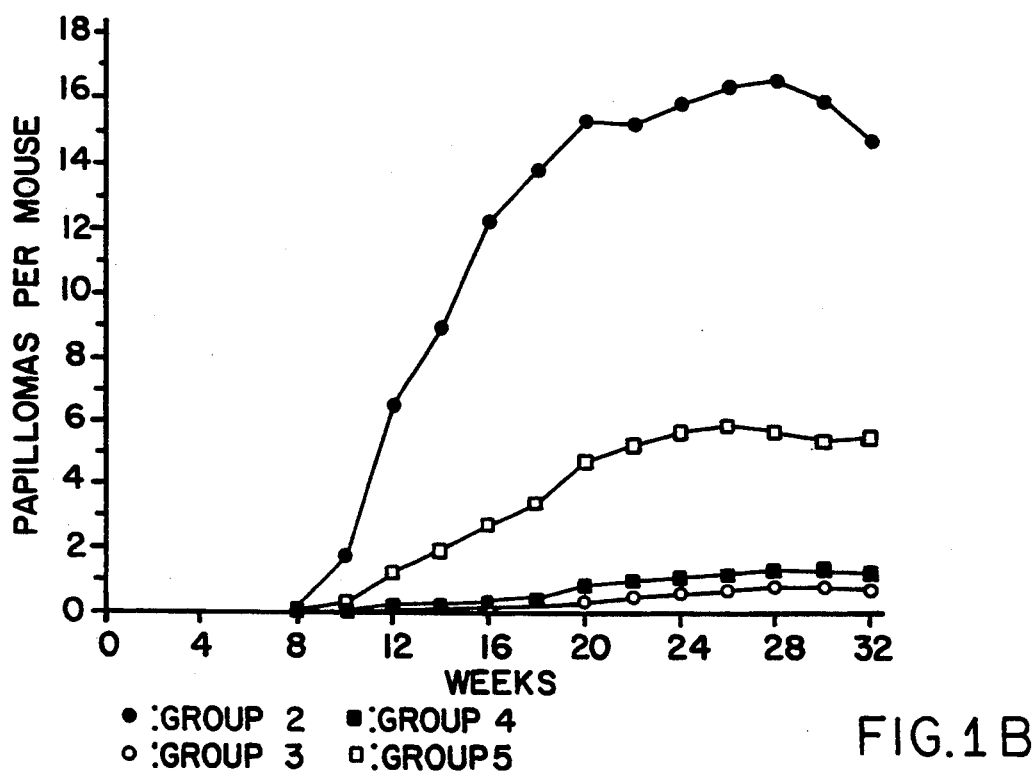

The topical application of 8.1 nmol PMA twice/week for 20 weeks induced tumors in 97–100% of the experimental animals by the 20th week (FIG. 1A; group 2). In the positive control group (group 2), the maximum of the average number of papillomas was 16.5/mouse (after 28 weeks of treatment). Prostratin (2.56 μmol/treatment; twice/week; for 20 weeks) showed neither complete carcinogenic nor tumor promoting activity, i.e., no tumors appeared in any of the groups (groups 6 and 7) with the aforesaid treatment schedule whether they had been initiated with 20 nmol DMBA or not.

These results clearly demonstrate the significant inhibiting effect of prostratin on neoplasia and tumor promotion.

TABLE 1

Treatment Schedule - First Set of Experiments

| Group | Initiation (day 1) | First Pretreatment (day 15) | Promotion (weeks 3–22, twice/week, 15 min difference between the two treatments in the designated order, from day 17) |
|---|---|---|---|
| 1 | DMBA (20 nmole) | 100 μl acetone | 100 μl acetone/100 μl acetone |
| 2 | DMBA (20 nmole) | 100 μl acetone | 100 μl acetone/PMA (8.1 nuole) |
| 3 | DMBA (20 nmole) | prostratin (256 nmole) | prostratin (2.56 μmole)/PMA (8.1 nmole) |
| 4 | DMBA (20 nmole) | prostratin (256 nmole) | prostratin (256 nmole)/PMA (8.1 rmole) |
| 5 | DMBA (20 nmole) | prostratin (256 nmole) | prostratin (25.6 nmole)/PMA (8.1 nmole) |
| 6 | DMBA (20 nmole) | prostratin (256 nmole) | prostratin (2.56 μmole)/100 μl acetone |
| 7 | 200 μl acetone | prostratin (256 nmole) | prostratin (2.56 μmole)/100 ml acetone |

During this evaluation, papillomas were counted every second week. On the 5th, 10th, and 20th week after the first PMA treatment, two mice per group were sacrificed for histological examinations which are described in Example 5.

According to previous results (Szallasi et al., Cancer Res., 51, 5355–5360 (1991) and Szallasi et al., Carcinogenesis 13, 2161–2167 (1992)), multiple prostratin pretreatments of 2.56 μmol were required for complete inhibition of PMA-induced chronic and acute hyperplasia in CD-1 mouse skin. The presumed effective doses of prostratin were estimated to be in the same dose range. This proved to be a significant underestimation of the antipromoting potency of prostratin. The percent of mice with papillomas and the number of papillomas per mouse versus the weeks of treatment were plotted as graphs constituting FIGS. 1A and 1B, respectively, for the groups of mice treated twice/week at 15 min inter- Example 2

This example demonstrates the in vivo efficacy of the present inventive method by illustrating the inhibition by prostratin and dPP of neoplasia and tumor promotion in animals.

This second set of experiments was carried out in a manner similar to the first set of experiments set out in Example 1, except that thirteen groups of 40 mice (groups 8 and 10–21) and one group of 100 mice (group 9) were established. The initiation process and general procedure were the same in the two sets of experiments; however, the pretreatment involved administering to the mice either 100 μl acetone, 256 nmol prostratin, or 2.14 nmol dPP. The promotion involved the administration of various combinations and concentrations of acetone, PMA, prostratin, and dPP to the initiated skin area. The precise treatment schedule is set forth in Table 2.

TABLE 2

Treatment Schedule - Second Set of Experiments

| Group | Initiation (day 1) | First Pretreatment (day 15) | Promotion (weeks 3–22, twice/week, 15 min difference between the two treatments in the designated order, from day 17) |
|---|---|---|---|
| 8 | DMBA (20 nmole) | 100 μl acetone | 100 μl acetone/100 μl acetone |
| 9 | DMBA (20 nmole) | 100 μl acetone | 100 μl acetone/PMA (8.1 nmole) |
| 10 | DMBA (20 nmole) | dPP (2.14 nmole) | dPP (21.4 nmole)/100 μl acetone) |
| 11 | DMBA (20 nmole) | dPP (2.14 nmole) | dPP (21.4 nmole)/PMA (8.1 nmole) |
| 12 | DMBA (20 nmole) | dPP (2.14 nmole) | dPP (2.14 nmole)/PMA (8.1 nmole) |

TABLE 2-continued

Treatment Schedule - Second Set of Experiments

| Group | Initiation (day 1) | First Pretreatment (day 15) | Promotion (weeks 3-22, twice/week, 15 min difference between the two treatments in the designated order, from day 17) |
|---|---|---|---|
| 13 | DMBA (20 nmole) | dPP (2.14 nmole) | dPP (214 pmole)/PMA (8.1 nmole) |
| 14 | DMBA (20 nmole) | dPP (2.14 nmole) | dPP (21.4 pmole)/PMA (8.1 nmole) |
| 15 | DMBA (20 nmole) | dPP (2.14 nmole) | dPP (2.14 pmole)/PKA (8.1 nmole) |
| 16 | DMBA (20 nmole) | prostratin (256 nmole) | prostratin (256 pmole)/PMA (8.1 nmole) |
| 17 | DMBA (20 nmole) | prostratin (256 nmole) | prostratin (25.6 nmole)/PMA (8.1 nmole) |
| 18 | DMBA (20 nmole) | prostratin (256 nmole) | prostratin (2.56 nmole)/PMA (8.1 nmole) |
| 19 | DMBA (20 nmole) | prostratin (256 nmole) | prostratin (256 pmole)/PMA (8.1 nmole) |
| 20 | DMBA (20 nmole) | prostratin (256 nmole) | prostratin (25.6 pmole)/PNA (8.1 nmole) |
| 21 | 100 µl acetone | dPP (2.14 nmole) | dpp (21.4 nmole)/100 µl acetone |

During this evaluation, papillomas were counted every second week. On the 7th, 12th, and 22nd week (i.e., 5, 10, and 20 weeks after the first PMA treatment), two mice per group were sacrificed as in Example 1 for histological examinations which are described in Example 5.

Figure 2A:
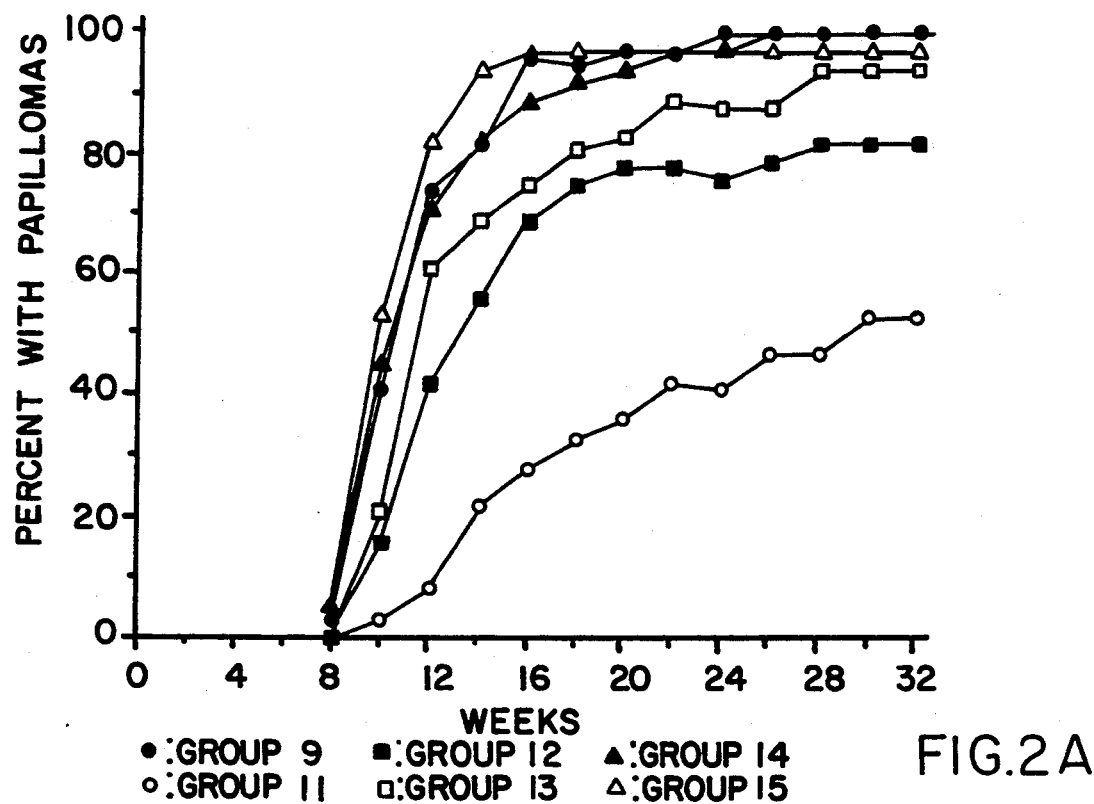
FIGS. 2A–2D are graphs illustrating the inhibition by prostratin and dPP of tumor promotion.
Figure 2B:
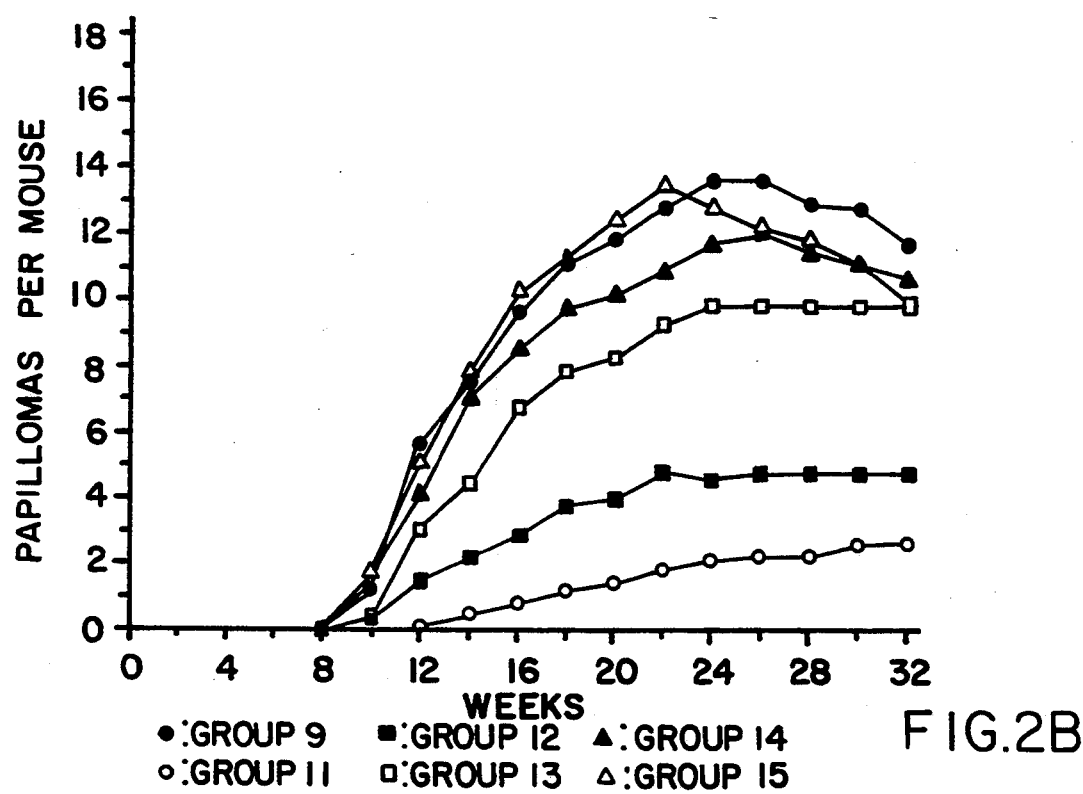

The percent of mice with papillomas and the number of papillomas per mouse versus the weeks of treatment with dPP were plotted as graphs constituting FIGS. 2A and 2B, respectively, for the groups of mice treated twice/week at 15 min intervals with the following doese: (●) 100 µl acetone/8.1 nmol PMA (group 9), (○) 21.4 nmol dPP/8.1 nmol PMA (group 11) (■) 2.14 nmol dPP/8.1 nmol PMA (group 12), (□) 214 pmol dPP/8.1 nmol PMA (group 13), (▲) 21.4 pmol dPP/8.1 nmol PMA (group 14), and (△) 2.14 pmol dPP/8.1 nmol PMA (group 15). The percent of mice with papillomas and the number of papillomas per mouse versus the weeks of treatment with prostratin were plotted as graphs constituting FIGS. 2C and 2D, respectively, for the groups of mice treated twice/week at 15 min intervals with the following doses: (●) 100 µl acetone/8.1 nmol PMA (group 9), (○) 256 nmol prostratin/8.1 nmol PMA (group 16), (■) 25.6 nmol prostratin/8.1 nmol PMA (group 17), (□) 2.56 nmol prostratin/8.1 nmol PMA (group 18), (▲) 256 pmol prostratin/8.1 nmol PMA (group (19), and (△) 25.6 pmol prostratin/8.1 nmol PMA (group 20). The percent with papillomas is defined as the percentage of surviving animals bearing one or more papillomas at every second week (FIGS. 2A and 2C), while the number of papillomas per mouse is defined as the total number of papillomas counted divided by the total number of mice surviving every second week (FIGS. 2B and 2D).

Figure 2C:
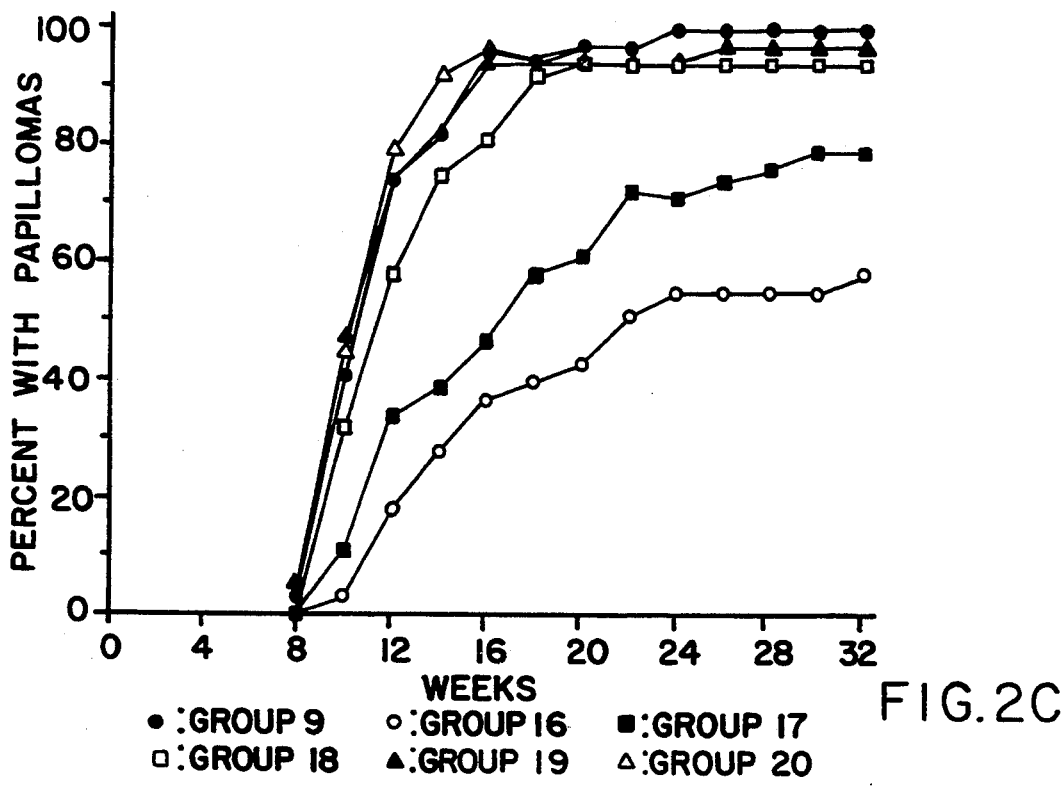
Figure 2D:
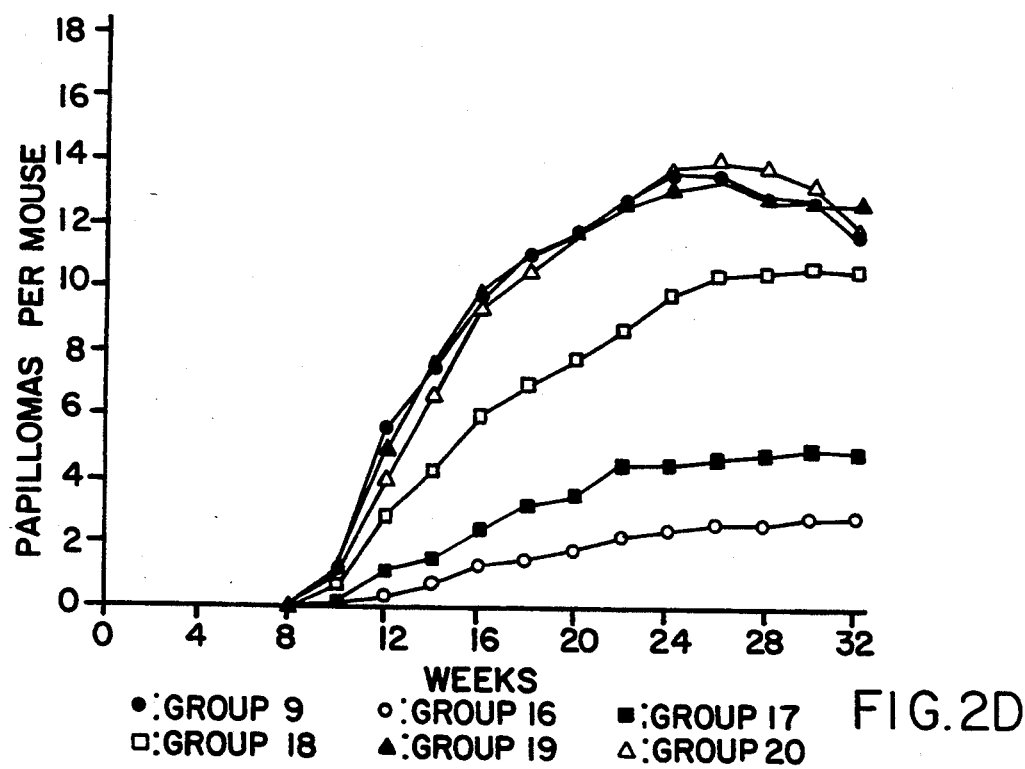

The topical administration of 8.1 nmol PMA twice/week for 20 weeks induced tumors in 97–100% of the experimental animals by the 20th week (FIGS. 2A and 2C; group 9). In the positive control group (group 9), the maximum of the average number of papillomas was 13.9/mouse (after 26 weeks of treatment). In the manner observed for prostratin in Example 1, dPP (21.4 nmol/treatment; twice/week; for 20 weeks) showed neither complete carcinogenic nor tumor promoting activity, i.e., no tumors appeared in any of the groups (groups 10 and 21) with the aforesaid treatment schedule whether they had been initiated with 20 nmol DMBA or not.

These results confirm the significant inhibiting effect of prostratin on neoplasia and tumor promotion and, further, clearly demonstrate the significant inhibiting effect of dPP on neoplasia and tumor promotion.

Example 3

This example demonstrates and evaluates the dose-dependent nature of prostratin and dPP treatments on the in vivo inhibition of neoplasia and tumor promotion in animals.

When PMA application was preceded by pretreatment with different doses of either prostratin or dPP in Examples 1 and 2, both the average number of papillomas and the tumor incidence were reduced in a dose-dependent manner. The highest dose of prostratin pretreatment (2.56 µmol/treatment) reduced the average number of papillomas 96% (23-fold), and reduced incidence of tumor from 97% to 40%, relative to the positive control group (compare groups 2 and 3 in FIGS. 1A and 1B). A dose of 21.4 nmol dPP/treatment reduced the average number of papillomas 86% (7-fold) with a decrease in the tumor incidence from 97% to 47% relative to the positive control group (compare groups 9 and 11 in FIGS. 2A and 2B).

Figure 3A:
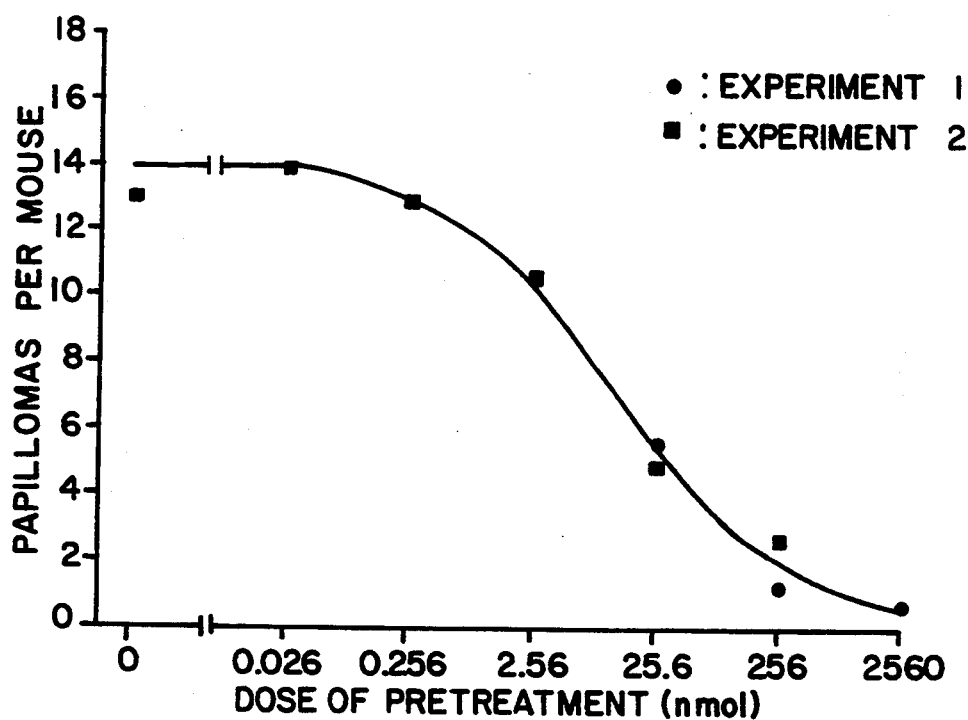
FIGS. 3A and 3B are graphs illustrating the dose-dependent inhibition by prostratin and dPP of tumor promotion.
Figure 3B:
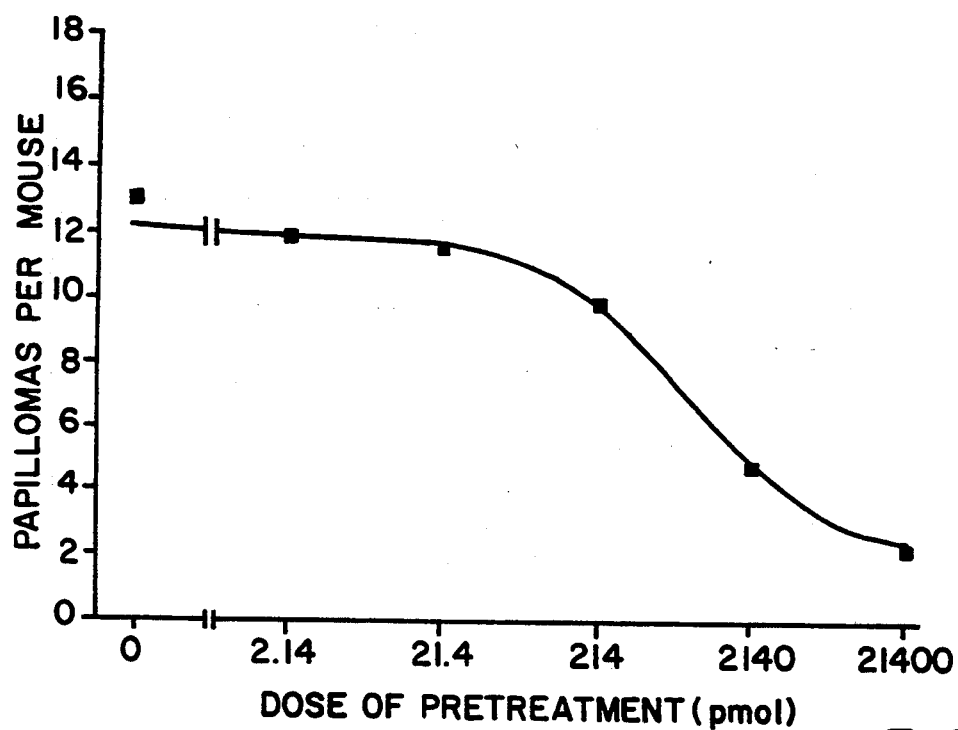

The data obtained in Examples 1 and 2 were converted into dose response curves at week 26, when all groups reached a plateau in the level of both tumor incidence and average number of papillomas. The data was separately plotted as the average number of papillomas per mouse versus dose of pretreatment for both prostratin and dPP in FIGS. 3A and 3B, respectively. Since the results obtained from groups of identical (prostratin) treatments in the first and second set of experiments in Examples 1 and 2 were very similar, the data for these treatments were pooled in determining the dose response curve of the prostratin treated groups ploted in FIG. 3A, wherein the symbol ● corresponds to the data from the first set of experiments in Example 1 and the symbol ■ corresponds to the data from the second set of experiments in Example 2. Since dPP was not administered in the first set of experiments in Example 1, and only in the second set of experiments in Example 2, there was no pooling of the dPP treatment data plotted in FIG. 3B. The inhibitory effect of both prostratin and dPP was dose-dependent. The $ID_{50}$ was 11 nmol/pretreatment for prostratin (FIG. 3A), and the $ID_{50}$ was 0.8 nmol/pretreatment for dPP (FIG. 3B). Although maximal inhibition of tumor promotion was accompanied by a block of epidermal hyperplasia, significant inhibition of tumor induction was observed at doses without any apparent effect on the PMA-induced hyperplasia.

The analysis of the data demonstrates the dose-dependency of treatments with 12-deoxyphorbol 13-monoesters in the present inventive method.

Example 4

This example further confirms the inhibitory effect of dPP on neoplasia and tumor promotion by evaluating different treatment regimens.

According to previous experiments, two 12-deoxyphorbol monoester pretreatments were needed for maximal inhibition of acute hyperplasia (Szallasi et al., *Cancer Res.*, 51, 5355–5360 (1991); Szallasi et al., *Carcinogenesis* 13, 2161–2167 (1992)). In the optimal protocol, the first pretreatment preceded the second one by 24–48 hours, and the dose of the first treatment was 10-fold lower than that of the second pretreatment. Since the mechanistic basis for this optimal short term schedule is unknown, several variants for the neoplasia and tumor promotion experiments in Examples 1 and 2 were evaluated.

The underlying concept was that the effect of the initial low dose of 12-deoxyphorbol might be lost as the duration of the experiment was extended using the procedures set out in Examples 1 and 2. For an additional group of 40 mice (group 22), the schedule included a first, low dose dPP pretreatment (2.14 nmol/treatment) every week, but otherwise the treatment pattern was the same as in Example 2. In two additional groups (groups 23 and 24), a single, 2-fold increased dose (16.2 nmol/treatment) of PMA treatment/week was used for promotion. Every PMA treatment was preceded by a lower dose dPP pretreatment (2.14 nmol/treatment) at a 48 h interval and a higher dose dPP pretreatment (21.4 nmol/treatment) at a 15 min interval. This latter protocol allowed a larger interval between the treatment with PMA and the subsequent low dose treatment with dPP. The precise treatment schedules are set forth in Tables 3 and 4.

TABLE 3

Treatment Schedule - Third Set of Experiments

| Group | Initiation | Pretreatment (Every Thursday, week 3–22) (from day 15) | Promotion (Every Friday and Monday, weeks 3–22, 15 min difference between the two treatments in the designated order) |
|---|---|---|---|
| 22 | DMBA (20 nmole) | dPP (2.14 nmole) | dPP (21.4 nmole)/PMA (8.1 nmole) |

TABLE 4

Treatment Schedule - Fourth Set of Experiments

| Group | Initiation | Pretreatment (Every Wednesday, week 3–22) (from day 15) | Promotion (Every Friday and Monday, weeks 3–22, 15 min difference between the two treatments in the designated order) |
|---|---|---|---|
| 23 | DMBA (20 nmole) | dPP (2.14 nmole) | dPP (21.4 nmole)/PMA (16.2 nmole) |
| 24 | DMBA (20 nmole) | 100 μl acetone | 100 μl acetone/PMA (16.2 nmole) |

During this evaluation, papillomas were counted every second week. On the 7th, 12th, and 22nd week (i.e., 5, 10, and 20 weeks after the first PMA treatment), two mice per group were sacrificed as in Example 1 for histological examinations which are described in Example 5.

Figure 4A:
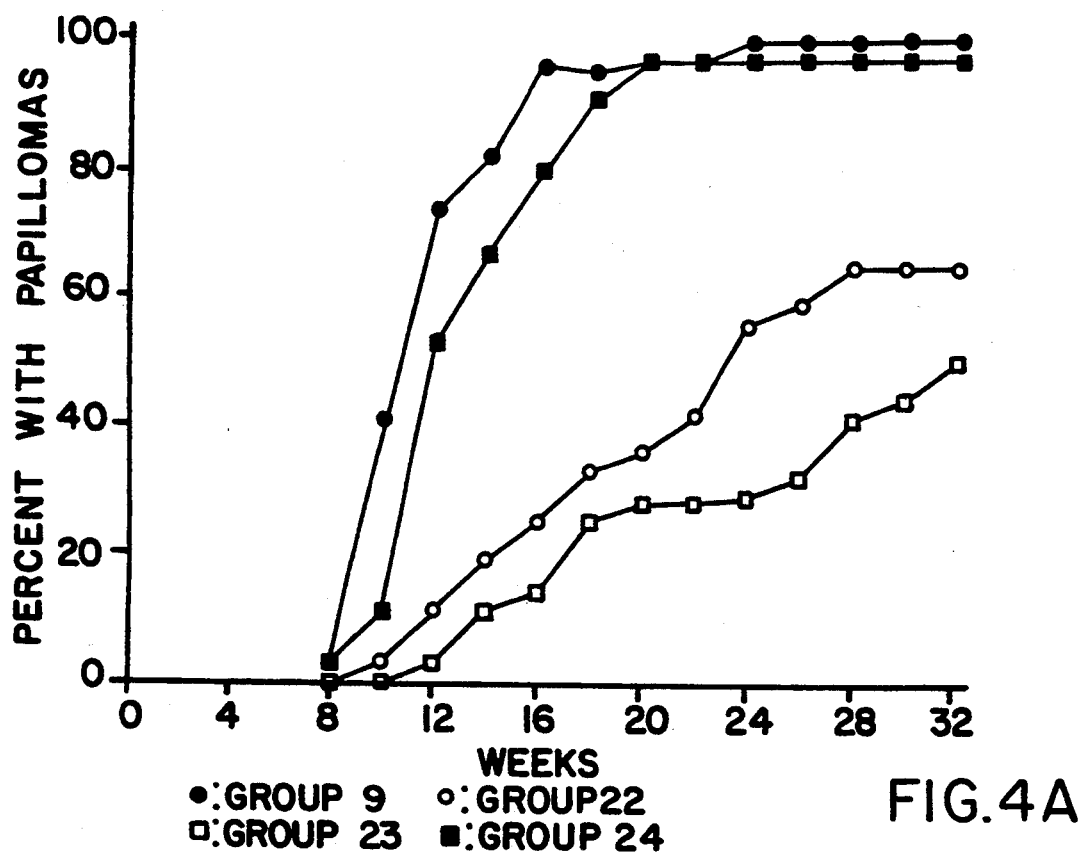
FIGS. 4A and 4B are graphs illustrating the inhibition by multiple dPP treatments of tumor promotion.
Figure 4B:
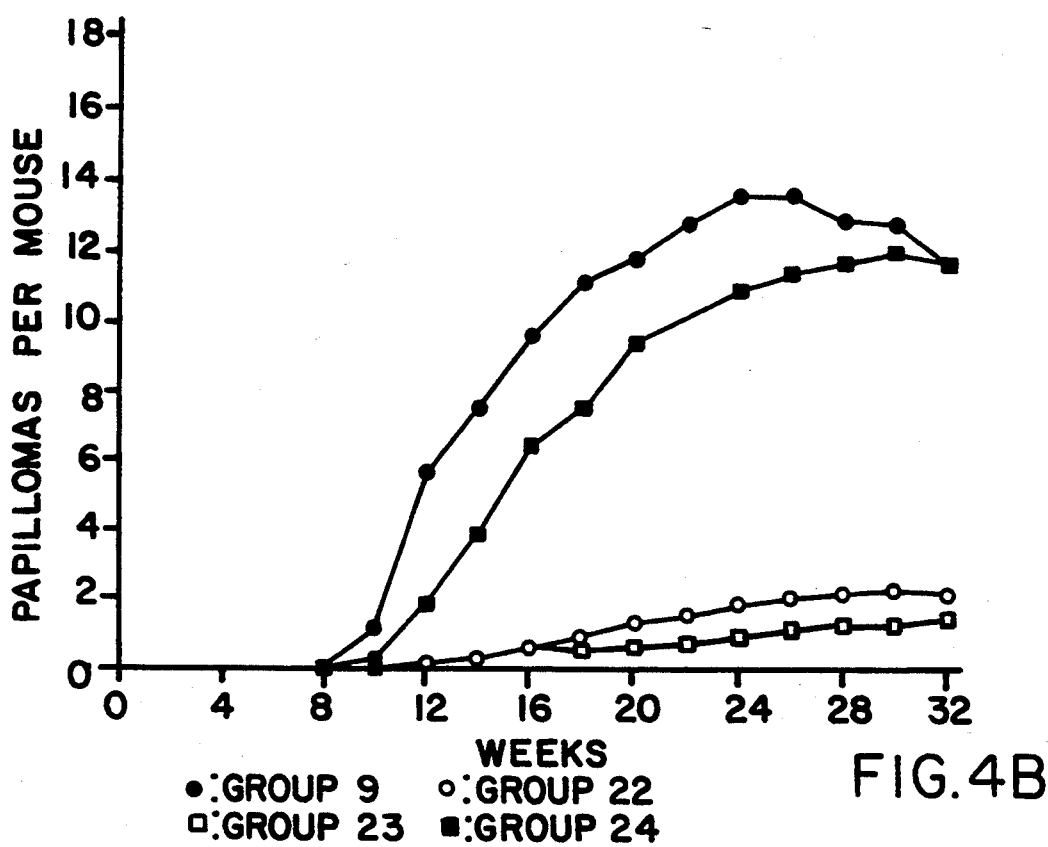

The percent of mice with papillomas and the number of papillomas per mouse versus the weeks of treatment were plotted as graphs constituting FIGS. 4A and 4B, respectively, for the groups of mice treated twice/week at 15 min intervals with the following doses: (●) 100 μl acetone/8.1 nmol PMA twice weekly (group 9), (○) 21.4 nmol dPP/8.1 nmol PMA twice weekly (group 22), (□) 21.4 nmol dPP/16.2 nmol PMA once weekly (group 23), and (■) 100 μl acetone/16.2 nmol PMA once weekly (group 24). Group 9 (●) is the control for group 22 (○), while group 24 (■) is the control for group 23 (□).

As illustrated in FIG. 4, the variation of the schedule did not appreciably altered the inhibitory potency of the dPP pretreatments.

Example 5

This example presents the results of the histological examinations performed on the sacrificed mice of Examples 1, 2, and 4 to assess hyperplasia.

As regards the set of experiments in Example 1, on the 5th, 10th, and 20th week after the first PMA treatment, two mice per group were sacrificed for histological examinations. The dorsal skin of two mice from each group was removed and fixed in either Bouin fixative or 70% ethanol. It was then sectioned and stained with hematoxylin-eosin by American Histolabs, Gaithersburg, Md. Under each set of conditions, two portions of the treated skin were excised per animal, and three sections were prepared from each portion of skin.

As regards the sets of experiments in Examples 2 and 4, on the 7th, 12th, and 22nd week (i.e., 5, 10, and 20 weeks after the first PMA treatment), two mice per group were sacrificed for histological examinations as in the same manner described above.

The chronic PMA treatment used for tumor promotion induced very significant hyperplasia in the positive control animals (group 9). After 7 and 12 weeks, of treatment significant inhibition of hyperplasia was detected in those groups in which the reduction of the average number of papillomas was the most prominent, namely in groups with 256 nmol prostratin or 21.4 nmol dPP pretreatment (groups 11, 16, 22, and 23). No inhibition could be observed in those groups with less significant inhibition of the number of papillomas. After 22 weeks of treatment, the evaluation of the sections became more complicated because of the frequent appearance of papillomas. However, in the above mentioned groups of maximal inhibition (groups 11, 16, 22, and 23), those parts of the sections which were far from papillomas or micropapillomas showed clear inhibition of hyperplasia.

All of the references cited herein (including publications, patents, patent applications, and the like) are hereby incorporated in their entireties by reference.

While this invention has been described with an emphasis upon a preferred embodiment, it will be obvious to those of ordinary skill in the art that variations of the preferred products and methods may be used and that it is intended that the invention may be practiced otherwise than as specifically described herein. Accordingly, this invention includes all modifications encompassed within the spirit and scope of the invention as defined by the following claims.

What is claimed is:

1. A method of inhibiting neoplasia and tumor promotion comprising administering to a mammal in need thereof an effective amount of a 12-deoxyphorbol 13-monoester.

2. The method of claim 1, wherein said ester is selected from the group consisting of formate, acetate, propionate, butyrate, pentanoate, hexanoate, benzoate, and phenylacetate.

3. The method of claim 2, wherein said ester is an acetate.

4. The method of claim 3, wherein said ester is a phenylacetate.

5. The method of claim 1, wherein said 12-deoxyphorbol ester is administered with a pharmaceutically acceptable carrier.

6. The method of claim 5, wherein said 12-deoxyphorbol 13-monoester is prostratin.

7. The method of claim 5, wherein said 12-deoxyphorbol 13-monoester is dPP.

8. The method of claim 1, wherein said neoplasia manifests as papilloma.

* * * * *